(12) United States Patent
Scheer et al.

(10) Patent No.: US 7,083,710 B2
(45) Date of Patent: Aug. 1, 2006

(54) GAS SENSOR, IN PARTICULAR A LAMBDA SENSOR

(75) Inventors: Heiner Scheer, Berqhuelen (DE); Hans-Martin Wiedenmann, Stuttgart (DE); Josef Hickl, Bietigheim-Bissingen (DE); Thomas Wahl, Pforzheim (DE); Gerhard Schneider, Pettstadt (DE); Harald Neumann, Oberriexingen (DE); Lothar Diehl, Stuttgart (DE); Jurgen Karle, Rutesheim (DE); Hans-Joerg Renz, Lewinfelden-Echterdingen (DE)

(73) Assignee: Robert Bosch GmbH, Stuttgart (DE)

( * ) Notice: Subject to any disclaimer, the term of this patent is extended or adjusted under 35 U.S.C. 154(b) by 490 days.

(21) Appl. No.: 10/169,235

(22) PCT Filed: Dec. 14, 2000

(86) PCT No.: PCT/DE00/04472

§ 371 (c)(1),
(2), (4) Date: Nov. 12, 2002

(87) PCT Pub. No.: WO01/50118

PCT Pub. Date: Jul. 12, 2001

(65) Prior Publication Data

US 2003/0089603 A1    May 15, 2003

(30) Foreign Application Priority Data

Dec. 29, 1999    (DE) ................. 199 63 566

(51) Int. Cl.
*G01N 27/409* (2006.01)
(52) U.S. Cl. ............. 204/427; 204/426; 73/23.32
(58) Field of Classification Search ........... 204/426, 204/427; 205/785; 73/23.31, 23.32; 427/58; 264/614; 156/89.12
See application file for complete search history.

(56) References Cited

U.S. PATENT DOCUMENTS

| | | | |
|---|---|---|---|
| 4,559,126 A | | 12/1985 | Mase et al. |
| 4,722,779 A | * | 2/1988 | Yamada et al. ............. 204/410 |
| 4,824,549 A | | 4/1989 | Hamada et al. |
| 5,314,604 A | | 5/1994 | Friese et al. |
| 5,378,345 A | * | 1/1995 | Taylor et al. ............... 204/421 |
| 5,421,984 A | | 6/1995 | Saito et al. |
| 6,036,841 A | * | 3/2000 | Kato et al. .................. 205/781 |

FOREIGN PATENT DOCUMENTS

| | | |
|---|---|---|
| DE | 37 44 206 | 8/1988 |
| DE | 44 01 749 | 7/1994 |

* cited by examiner

*Primary Examiner*—Kaj K. Olsen
(74) *Attorney, Agent, or Firm*—Kenyon & Kenyon LLP

(57) ABSTRACT

The reference air channel of a gas sensor or a lambda probe having a laminate body produced by printing technology is provided. The laminate body is produced by printing a suitably structured layer onto a neighboring layer, for example, by screen printing.

14 Claims, 2 Drawing Sheets

GAS SENSOR, IN PARTICULAR A LAMBDA SENSOR

This application is a 371 of PCT/DE00/04472, filed on Dec. 14, 2000, which claims priority to German application 199-63-566.8, filed on Dec. 29, 1999.

FIELD OF THE INVENTION

The present invention relates to a gas sensor, for example, a lambda probe, having a sintered ceramic laminate body, within which a reference air channel is arranged inside a layer of the laminate. A electric resistance heater is situated (or embedded) in the laminate on one side thereof, and an electrode arrangement is provided on the other side of the laminate, at least one reference electrode, which is gas-permeable in at least some areas, being arranged inside a bordering wall of the reference air channel, and a Nernst electrode, which is also gas-permeable in at least some areas, being acted upon by a gas to be sensed, in which the at least one reference electrode and the Nernst electrode are separated by a solid electrolyte layer, which is conductive and permeable to ions, for example, oxygen ions.

BACKGROUND INFORMATION

Exhaust systems in modern internal combustion engines may be provided with catalysts for catalytic decomposition of noxious exhaust gases, for example, those occurring in motor vehicles. For good functioning of the catalysts, air and fuel should be supplied to the engine in a predetermined ratio. For this purpose, engine controls are provided, which may be connected to a lambda probe. The signals of the lambda probe indicate the composition of the exhaust gases and thus permit the engine control to optimally regulate the ratio of fuel and combustion air for the catalyst.

In this regard, two concepts are described below.

The first concept attempts to achieve a stoichiometric combustion, i.e., when the quantity of oxygen in the combustion air corresponds exactly to the oxygen demand for complete combustion of the fuel supplied. In this case, the engine is not operated with an oxygen excess ($\lambda>1$) or an oxygen deficiency ($\lambda<1$). This type of operation may be characterized by $\lambda=1$.

For stoichiometric combustion, narrowband lambda probes may be sufficient for exhaust gas sensing, the Nernst electrode being acted upon essentially directly by the exhaust gas.

This engine control considers the effect that an electric voltage, which is generated by diffusion of oxygen ions and is detectable between the reference electrode and the Nernst electrode, changes in value in the range of $\lambda=1$. Thus, a signal that indicates a deviation from the desired operation of stoichiometric combustion is available. This signal may indicate both a deficiency of oxygen as well as an excess of oxygen, with respect to stoichiometric combustion.

Such sensors are referred to in German Published Patent Application No. 44 01 749, for example.

The second concept attempts to achieve operation of the combustion engine predominantly with an excess of oxygen in combustion, since this may allow a significant reduction in fuel consumption. However, harmful nitrogen oxides, which may form in combustion with excess oxygen, may be absorbed by storage catalysts in the exhaust line of an automotive engine only for a limited period of time. Before the storage capacity of these storage catalysts is depleted, operation of the engine must be switched briefly to combustion with an oxygen deficiency, to permit reduction of the nitrogen oxides previously stored in the catalyst. These nitrogen oxides may accumulate, for example, due to incompletely burned fuel constituents entering the exhaust gas line. The engine control should therefore be switched repeatedly and intermittently between a mode of operation that is predominant over a period of time in which the values of $\lambda$ are above 1 and a relatively short-term mode of operation, in which the values of $\lambda$ are less than 1.

Broadband lambda probes may be necessary for such intermittent operation with greatly varying values of $\lambda$.

With such lambda probes, the Nernst electrode is arranged in a separate chamber, which communicates with the exhaust gas stream via a diffusion zone in the body of the probe. In addition, an internal pump electrode, which is situated inside this chamber, which may be connected electrically to the Nernst electrode, and which cooperates with an external pump electrode through a solid electrolyte layer, is essentially directly exposed to the exhaust gas stream. If an external electric voltage is applied between the two pump electrodes, both of which may be gas-permeable in at least some areas, an oxygen ionic current is generated between the pump electrodes in a direction depending on the polarity of the applied voltage and with an amperage depending on the electric potential difference. This external voltage permits the control of the diffusion stream of the exhaust gases into the diffusion chamber, for example, by a regulator which adjusts the external electric voltage between the pump electrodes and the electric current occurring between the pump electrodes because of the oxygen ionic current, so that an electric voltage having a predetermined setpoint is maintained between the reference electrode and the Nernst electrode. Thus, the polarity and amperage of the electric current between the pump electrodes may produce a signal in correlation with the composition of the exhaust gases and thus with the $\lambda$ values.

Such probes are referred to in German Published Patent Application No. 37 44 206, for example.

The probes described above should be heated during operation to generate a signal that may be analyzed. Therefore, lambda probes and other gas sensors may have an electric resistance heater, which in the case of a probe body formed by a laminate, may be situated on or between layers of the laminate.

SUMMARY OF THE INVENTION

In an exemplary embodiment according to the present invention, the reference air channel is situated in a structured layer or in a layer arrangement produced by printing technology.

It is believed that this offers the advantage in that various desired shapes, including small parts, may be possible for the reference air channel in comparison with a type of production, for example, in which parts are punched out of a green ceramic film.

For example, the contours of the reference air channel may be adapted to the contours of the electric resistance heater, which may meander, or in a top view of the layer planes they may be removed by an entrance hole for the exhaust gases passing through the probe body perpendicular to the layer planes.

In addition, the reference air channel may be divided like a fan for the admission of the reference air and/or to position the layer or layer arrangement forming the reference air channel on the longitudinal edges, the layer or layers of the layer arrangement optionally being broken down into non-coherent parts, without thereby increasing the manufacturing complexity.

Due to the smaller cross sections of the reference air channel, which may be possible with production by printing technology, and due to the comparatively small height of this channel perpendicular to the planes of the layer, a good heat conducting connection is created between the parts of the probe body on both sides of the layer or layer arrangement accommodating the reference air channel, so that the thermal stresses occurring at the start of heating within the probe body may remain low and/or the probe body may be rapidly heated.

Moreover, the reference air channel may be filled with a porous mass, thus permitting a better heat transfer between the laminate parts on both sides of the reference air channel.

Production of the reference air channel by printing technology may be accomplished so that a negative pattern of the reference air channel is printed on the side of a layer carrying the heater or sheaths the heater, this side facing the reference air channel, and/or on the side (of the solid electrolyte layer arranged between the reference electrode and the Nernst electrode) carrying the reference electrode, this pattern being printed using a pasty material, for example, zirconium oxide paste, that hardens under heat.

In addition, the positive shape of the reference air channel may be printed with a pasty material that partially or completely burns off, forming a porous structure. This may guarantee, or at least make more probable, for example, that the reference air channel has a reproducible height perpendicular to the planes of the layer of the laminate.

In summary, an exemplary embodiment according to the present invention produces the reference air channel by technical printing, to reproducibly produce various desired filigree structures with a low manufacturing complexity.

DETAILED DESCRIPTION

Figure 1:
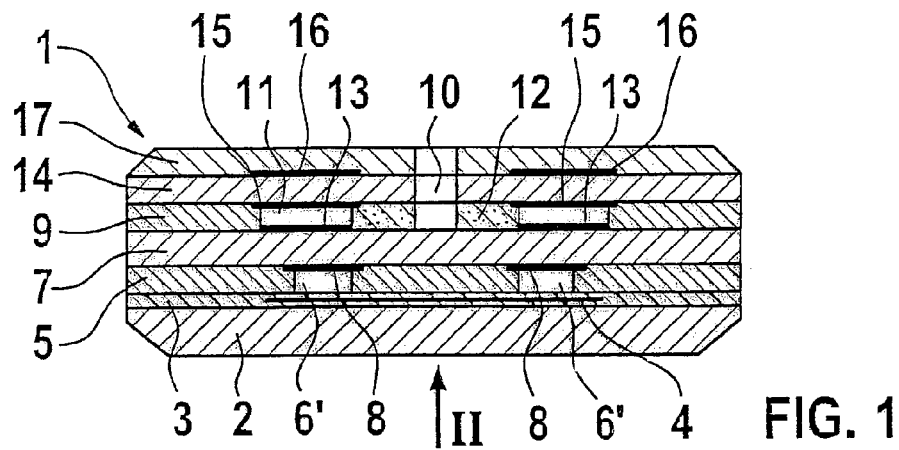
FIG. 1 is a cross sectional view through a broadband lambda probe across line I—I in FIG. 2 in an area of the end of the probe body projecting into the exhaust gas stream.
Figure 3:
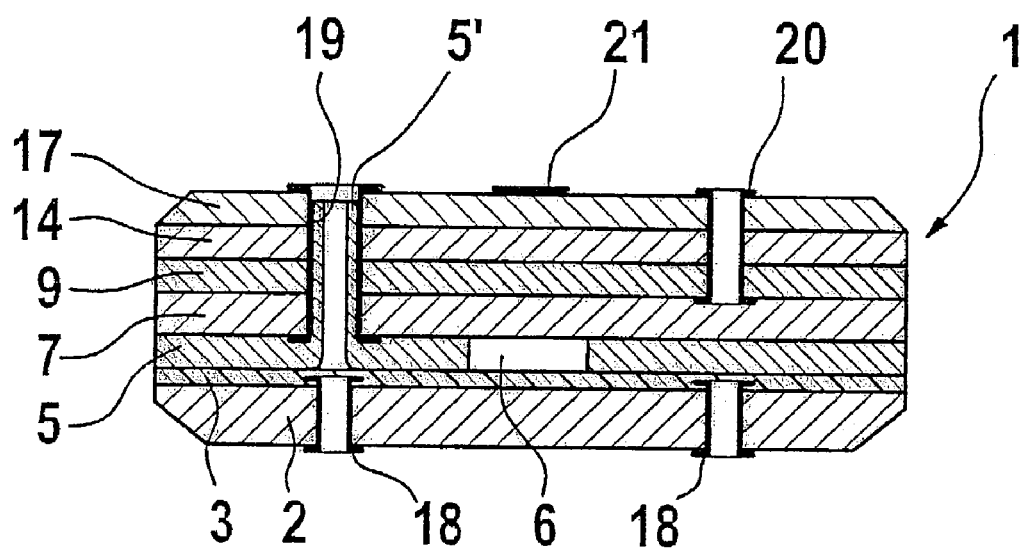
FIG. 3 is a cross sectional view of the end of the probe body on the reference air side parallel to the sectional plane of FIG. 1.

As shown in FIGS. 1 and 3, the lambda probe has a body 1 designed as a ceramic laminate. The layers of the laminate are applied or stacked green. After subsequent sintering, which may occur after or simultaneously with pressing of the laminate, a hard ceramic body 1 is produced.

A bottom layer 2 of a thicker film of zirconium oxide is provided, above which an electrically insulating double layer 3 is provided. An electric resistance heater 4 and respective printed conductors for the electric power supply are embedded within the double layer 3, above which a layer 5, which may be produced by screen printing, is structured. Layer 5 may be made of, for example, zirconium oxide paste. Within this layer, a reference air channel 6 is formed, an example of its outline being illustrated in FIG. 2 and described below. This reference air channel 6 has two end areas 6' communicating with one another in the area of the sectional plane of FIG. 1.

Above layer 5 a solid electrolyte layer 7 is provided, for example, as a zirconium oxide film, to which yttrium oxide has been added. At least in the area of end areas 6' of reference air channel 6, a gas-permeable, laminar reference electrode 8 made of a porous platinum material is situated on the side of layer 7 facing reference air channel 6 or between layers 5 and 7. This electrode 8 is connected to a terminal contact on body 1, by an adjoining laminar printed conductor 8', as described below. (see FIG. 2).

Above solid electrolyte layer 8, a thin layer 9 is provided, which is structured by printing technology and may be made of, for example, zirconium oxide paste. This layer 9 has a large recess, which is arranged centrally with respect to an exhaust gas admission hole 10 passing through body 1 perpendicular to its layers. A porous material 12 is deposited within this recess, leaving an annular space 11.

In the area of annular space 11, solid electrolyte layer 7 has a gas-permeable laminar Nernst electrode 13 made of a porous platinum material.

Another solid electrolyte layer 14, for example, a zirconium oxide film containing yttrium oxide, is provided above layer 9, i.e., porous material 12. On its side facing annular space 11 and on its side facing away from annular space 11, layer 14 has gas-permeable inner and outer pump electrodes 15 and 16 made of a platinum material that is porous in at least some areas. These electrodes 15 and 16 are shaped so that they at least essentially cover annular space 11 as seen from the top of the layers of body 1. A gas-permeable protective layer 17 is also provided above layer 14.

For resistance heater 4 and various electrodes 8, 13, 15 and 16 to be electrically accessible from the outside, contact lugs (not shown) are situated on the reference air-side end of body 1. These lugs, which may be produced by printing technology, are connected to resistance heater 4 or electrodes 8, 13, 15 and 16 via through-contacts passing through one or more layers and adjoining conductors running between adjacent layers.

As shown in FIG. 3, two through-contacts 18 passing through bottom layer 2 are provided for connecting electric resistance heater 4. These through-contacts 18 may have, for example, an annular or cylindrical shape, as shown in FIG. 3.

In addition, a through-contact 19 designed in an annular or cylindrical shape and passing through the layers above layer 5 is provided for reference electrode 8. Contacts 18 and 19 may also be arranged coaxially.

To guarantee, or at least make more probable, reliable electric insulation, despite the small thickness of layer 5 and the small distance between the facing ends of contact 19 and coaxial contact 18, the electrically insulating material of layer 5 is drawn into through-contact 19, so that the bottom end of through-contact 19, as shown in FIG. 3, is covered by electrically insulating material.

A through-contact 20 passing through layers 9, 14 and 17 is electrically connected to Nernst electrode 13 and to internal pump electrode 15. External pump electrode 16 is connected to a contact 21 via a printed conductor (not shown) passing through protective layer 17.

Figure 2:
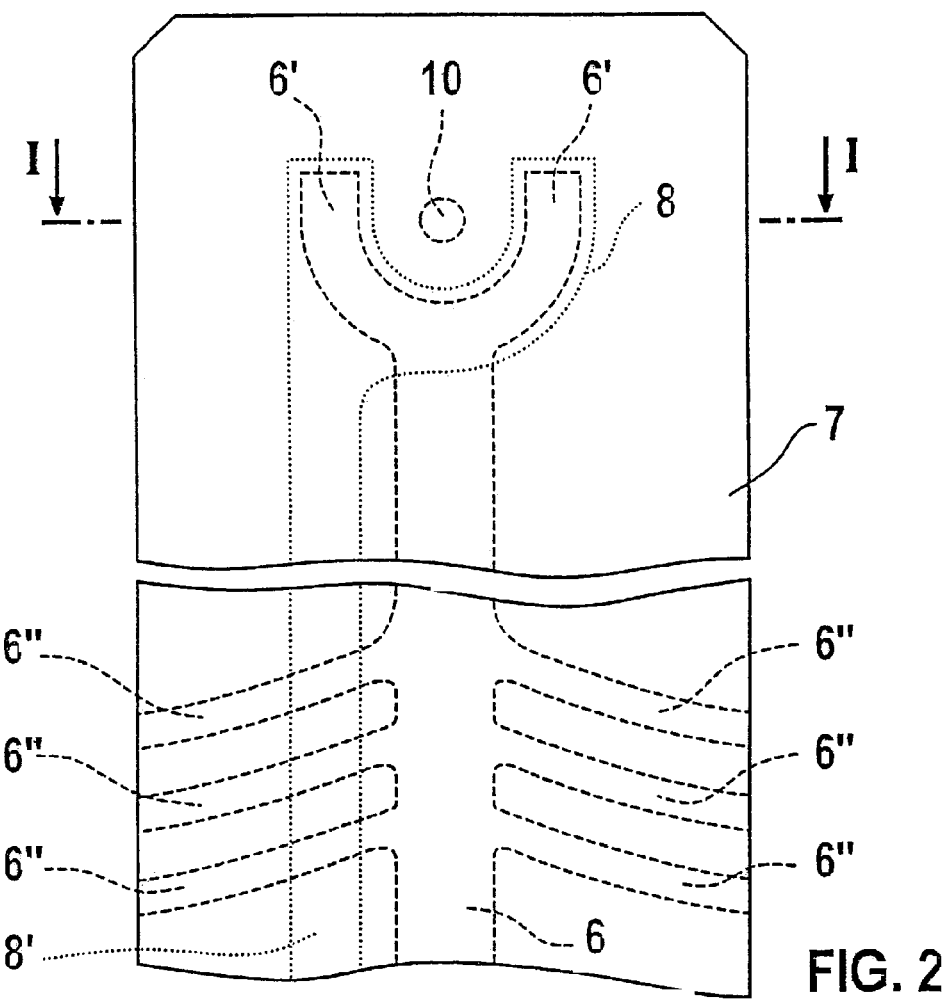
FIG. 2 is top view of the solid electrolyte layer between the reference electrode and the Nernst electrode as seen in a direction of arrow II in FIG. 1, showing the contours of the layer applied to the abovementioned layer by printing technology for the reference air channel.

The production and structuring of layer 5 on layer 7 by printing technology are described below with reference to FIG. 2.

Reference electrode 8 and respective printed conductor 8' are first printed on film layer 7, for example, by screen printing. Then, a negative image of reference air channel 6 and its end pieces 6' and any optional fan-like mouths 6" is applied with the material of layer 5. This may be performed, for example, by screen printing using appropriate masks. It should be noted that extremely fine filigree structures may be optionally produced in this manner.

If the coating of solid electrolyte layer 7 is performed with the material of layer 5, layer 7 is already stacked with the layers situated above layer 7, as shown in FIGS. 1 and 3. In addition, through-contact 19 is also positioned. Accordingly, the material of layer 5 may be drawn into the interior at through-contact 19, so that this interior space is covered by material 5', at least in the lower area, as shown in FIG. 3, and thus is reliably insulated electrically at a later point in time with respect to through-contact 18, which is coaxial with through-contact 19. This may guarantee, or at least make more probable, for example, that no conducting connection may be created between coaxial through-contacts 18 and 19 due to fouling.

A positive image of reference air channel 6 and its end pieces 6' and mouths 6" may optionally be printed onto layer 7 using a material, which dissolves, burns off, or forms a porous, highly gas-permeable structure when body 1 is sintered.

Layer 3 may be printed with the material of layer 5 in mirror image to layer 7. Also, optionally, layer 3 may be printed with the material provided for the positive image of reference air channel 6 and its parts 6' and 6". In this manner, layer 5 may be produced with a greater thickness.

The lambda probe described above functions as follows:

The end of body 1 having exhaust gas admission hole 10 is situated in the exhaust gas stream, that is, in an area communicating with the exhaust gas stream of an internal combustion engine, while the other end of body 1 is acted upon by reference air, for example, atmospheric air.

Reference air reaches end pieces 6' of the reference air channel through reference air channel 6 via its mouths 6". Exhaust gas passes through exhaust gas admission hole 10 to porous material 12, through which the exhaust gas diffuses into annular space 11.

When body 1 is sufficiently heated by electric resistance heater 4, an electric voltage may be detected between reference electrode 8 and Nernst electrode 13 and thus between through-contacts 19 and 20. The size of this voltage depends on the oxygen partial pressures within end pieces 6' of the reference air channel and within annular space 11. Specifically, the platinum material of aforementioned electrodes 8 and 13 promotes or permits the formation of oxygen ions, resulting in an ion diffusion in solid electrolyte layer 7, which depends on the concentration of oxygen ions on electrodes 8 and 13. This results in an electric potential difference between electrodes 8 and 13.

The oxygen partial pressure in annular space 11 may be controlled by applying an external electric voltage having a controllable polarity between pump electrodes 15 and 16. The corresponding voltage source is connected to through-contact 20, i.e., to contact 21. In this manner, an oxygen ion current is produced having an amperage and direction depending on the electric voltage and polarity of the external electric voltage. This ion current diffuses through solid electrolyte layer 14, since the platinum material of electrodes 15 and 16 forms oxygen ions. Thus, an electric current is detectable between pump electrodes 15 and 16.

A regulator may control the electric voltage and the electric current between pump electrodes 15 and 16, so that the electric voltage available between reference electrode 8 and Nernst electrode 13 corresponds to a fixed setpoint. The electric current available between pump electrodes 15 and 16 is a measure of the oxygen content of the exhaust gases relative to the reference air.

If external pump electrode 16 is at a positive electrical potential with respect to internal pump electrode 15, the prevailing operating conditions have $\lambda>1$. When the polarity is reversed, the prevailing operating conditions have $\lambda<1$, the measure of the electric current detectable between electrodes 15 and 16 correlating with the size of $\lambda$.

The values of $\lambda$ may be detected in a large value range.

In the case of narrow-band lambda probes, external protective layer 17 may be above Nernst electrode 13, that is, layers 9 and 14, and pump electrodes 15 and 16 may be omitted. In this case, the electric voltage detectable between electrodes 8 and 13 is a measure of the oxygen partial pressure of the exhaust gases.

Depending on the design of the lambda probes for narrow-band or broadband measurement, reference air channel 6, together with its parts 6' and 61", may be produced in the manner described above by deposition of structured layer 5 by printing technology.

The invention claimed is:

1. A gas sensor, comprising:
   a sintered ceramic laminate body including one of a structured layer and a structured layer arrangement, within which a reference air channel is arranged, the one of the structured layer and the structured layer arrangement being produced by a printing technology, and the reference air channel including a bordering wall;
   an electrically insulated electric resistance heater embedded in the laminate on one side of the laminate;
   an electrode arrangement arranged on another side of the laminate, the electrode arrangement including at least one reference electrode arranged inside the bordering wall of the reference air channel, the at least one reference electrode being gas permeable in at least selected portions, the electrode arrangement further including a Nernst electrode operable to be acted upon by a gas to be sensed, the Nernst electrode being gas permeable in at least selected portions; and
   a solid electrolyte layer separating the Nernst electrode from the at least one reference electrode, the solid electrolyte layer being conductive and permeable to ions,
   wherein the reference air channel includes mouths arranged in a fan like pattern, the mouths extending outwards towards at least one end of the one of the structured layer and the structured layer arrangement for admission of a reference air at the at least one end.

2. The gas sensor according to claim 1, further comprising:
   through-contacts passing through at least one layer of the body and connecting contacts situated on an outside of the body to one of the following:
   (a) the electrodes of the electrode arrangement, and
   (b) printed conductors electrically connected to the electrodes of the electrode arrangement,
   wherein the one of the structured layer and the structured layer arrangement does not include any of the at least one layer through which the through-contacts pass.

3. The gas sensor according to claim 1, wherein the solid electrolyte layer is conductive and permeable to oxygen ions.

4. The gas sensor according to claim 1, wherein the printing technology includes screen printing.

5. The gas sensor according to claim 1, wherein the reference air channel is filled with a porous material having gas permeable properties.

6. A gas sensor, comprising:
   a sintered ceramic laminate body including one of a structured layer and a structured layer arrangement, within which a reference air channel is arranged, the one of the structured layer and the structured layer arrangement being produced by a printing technology, and the reference air channel including a bordering wall;
   an electrically insulated electric resistance heater embedded in the laminate on one side of the laminate;
   an electrode arrangement arranged on another side of the laminate, the electrode arrangement including at least one reference electrode arranged inside the bordering wall of the reference air channel, the at least one reference electrode being gas permeable in at least selected portions, the electrode arrangement further including a Nernst electrode operable to be acted upon by a gas to be sensed, the Nernst electrode being gas permeable in at least selected portions;
   a solid electrolyte layer separating the Nernst electrode from the at least one reference electrode, the solid electrolyte layer being conductive and permeable to ions; and
   through-contacts passing through at least one layer of the body and connecting contacts situated on an outside of the body to one of the following:
      (a) the electrodes of the electrode arrangement, and
      (b) printed conductors electrically connected to the electrodes of the electrode arrangement,
   wherein the one of the structured layer and the structured layer arrangement does not include any of the at least one layer through which the through-contacts pass, and
   wherein the through contacts have ring shaped cross sections provided with an electrically insulating coating on an inside of the through contacts.

7. The gas sensor according to claim 6, wherein the gas sensor is a lambda probe.

8. The gas sensor according to claim 6, wherein the solid electrolyte layer is conductive and permeable to oxygen ions.

9. The gas sensor according to claim 6, wherein the printing technology includes screen printing.

10. The gas sensor according to claim 6, wherein the reference air channel further includes a core that extends along a length of the at least one of the structured layer and the structured layer arrangement, and parts including at least one of (a) at least one reference air inlet and (b) at least one end piece, the parts extending from the core, and wherein, in comparison to a size of a surface area of the one of the structured layer and the structured layer arrangement used by the reference air channel, large surface areas of the one of the structured layer and the structured layer arrangement are provided at the electric resistance heater in a vicinity of one of the reference air channel and the parts of the reference air channel, the large surface areas being operable to heat conductively couple the resistance heater to the electrolyte layer separating the Nernst electrode from the at least one reference electrode.

11. The gas sensor according to claim 6, wherein the reference air channel is filled with a porous material having gas permeable properties.

12. The gas sensor according to claim 6, further comprising:
   an admission opening for receiving the gas to be sensed, the admission opening passing through at least one layer of the body and being perpendicular to a plane of the laminate and arranged within the body,
   wherein the one of the structured layer and the structured layer arrangement does not include any of the at least one layer through which the admission opening passes.

13. The gas sensor according to claim 6, wherein the one of the layer and layer arrangement includes at least one short side and at least one long side, and the reference air channel opens outwardly towards at least one of the at least one long side of the one of the layer and layer arrangement including the reference air channel.

14. The gas sensor according to claim 6, wherein the one of the structured layer and the structured layer arrangement including the reference air channel is made of the same material as the electrically insulating coating.

* * * * *